(12) United States Patent
Klitmose

(10) Patent No.: US 6,537,251 B2
(45) Date of Patent: Mar. 25, 2003

(54) MEDICATION DELIVERY DEVICE WITH BENDED PISTON ROD

(75) Inventor: Lars Peter Klitmose, Gentofte (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/972,829

(22) Filed: Oct. 4, 2001

(65) Prior Publication Data

US 2002/0091358 A1 Jul. 11, 2002

Related U.S. Application Data

(60) Provisional application No. 60/240,898, filed on Oct. 17, 2000.

(30) Foreign Application Priority Data

Oct. 5, 2000 (DK) .......................................... 2000 01484

(51) Int. Cl.⁷ ................................................ A61M 5/20
(52) U.S. Cl. ...................................... 604/135; 604/131
(58) Field of Search ................................. 604/131, 132, 604/133, 134, 135, 151–155, 121, 246, 218; 128/DIG. 12

(56) References Cited

U.S. PATENT DOCUMENTS

| | | |
|---|---|---|
| 4,493,704 A | 1/1985 | Kirk et al. |
| 5,064,098 A | 11/1991 | Hill et al. |
| 5,261,882 A | 11/1993 | Sealfon |
| 5,637,095 A | 6/1997 | Nason et al. |

FOREIGN PATENT DOCUMENTS

| | | | |
|---|---|---|---|
| EP | 0 110 687 A1 | 11/1983 | ............ A61M/5/14 |
| WO | WO 95/09021 | 9/1994 | .......... A61M/5/315 |
| WO | WO 98/01173 | 6/1997 | .......... A61M/5/315 |

*Primary Examiner*—Manuel Mendez
(74) *Attorney, Agent, or Firm*—Marc A. Began, Esq.; Richard W. Bork, Esq.; Reza Green, Esq.

(57) ABSTRACT

The invention relates to: A portable medication delivery device (1) comprising a medication cartridge (11) having an outlet (111) and a movable piston (112), and a housing (12) for holding said cartridge, and a flexible piston rod (13) being operable to engage and displace said piston along an axis (113) of said cartridge, and guiding means (14) for bending said piston rod away from said axis, and actuating means (15), and driving means (16, 17) for transferring movement from said actuating means to said piston rod, said driving means including a driving wheel (17) for displacing the piston rod (13), said flexible piston rod comprising regularly spaced first members (330; 331; 332) adapted to mechanically cooperate with corresponding second members (171) on said driving wheel. The object of the present invention is to provide a medication delivery system that combines compactness with an improved accuracy. The problem is solved in that said flexible piston rod (13) exhibits a linear or approximately linear path between said driving wheel (17) and said piston (112). This has the advantage of yielding a compact, low-weight device with an improved dose accuracy. The invention may e.g. be used in injection or infusion devices for a person's self-treatment of a disease such as diabetes.

19 Claims, 7 Drawing Sheets

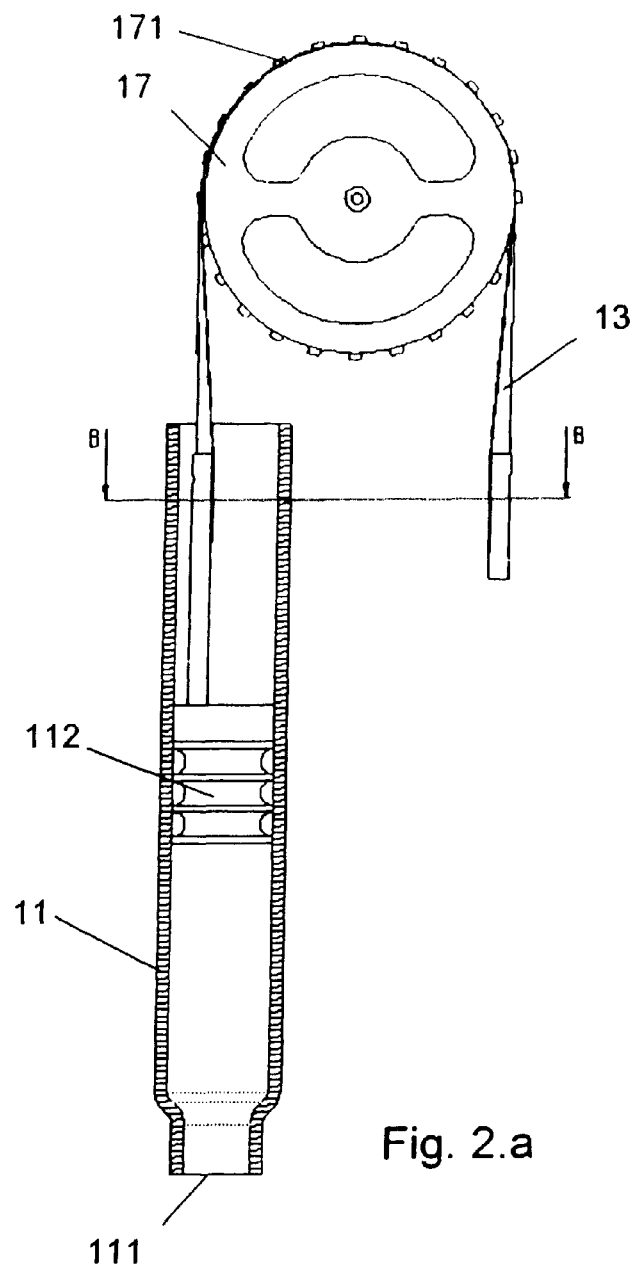
Fig. 2.a
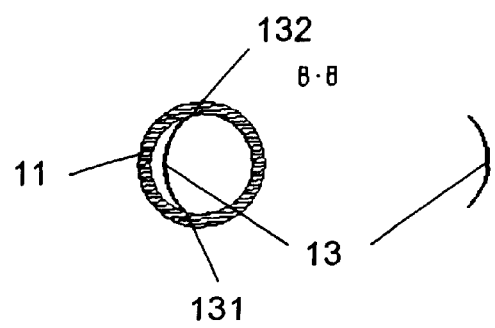
Fig. 2.b

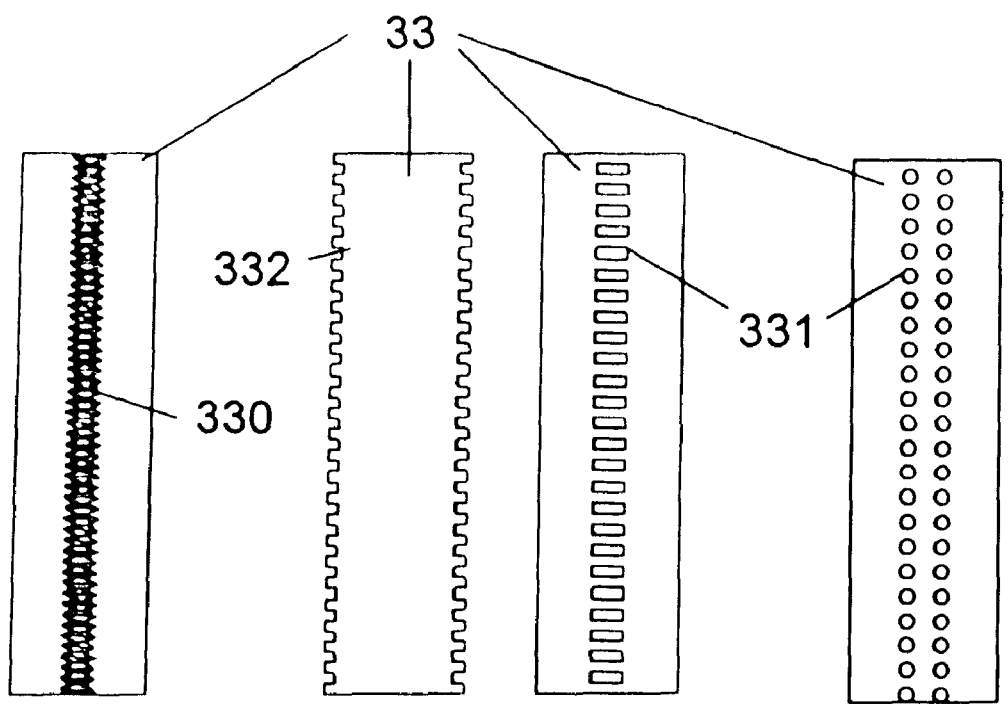
Fig. 3.a    Fig. 3.b    Fig. 3.c    Fig. 3.d

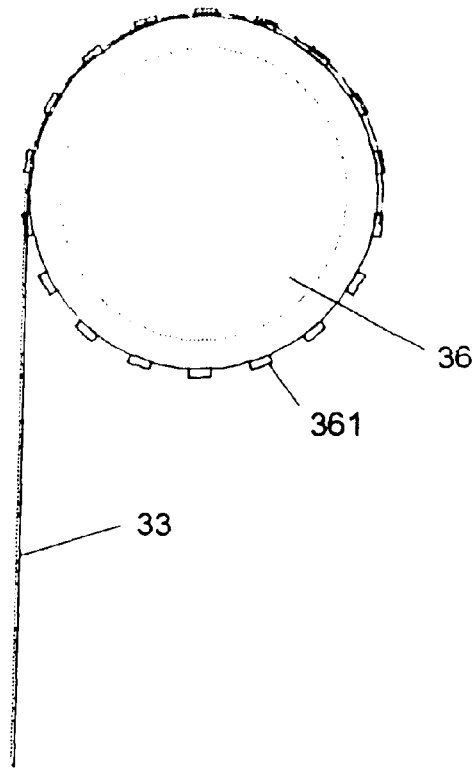
Fig. 4.a
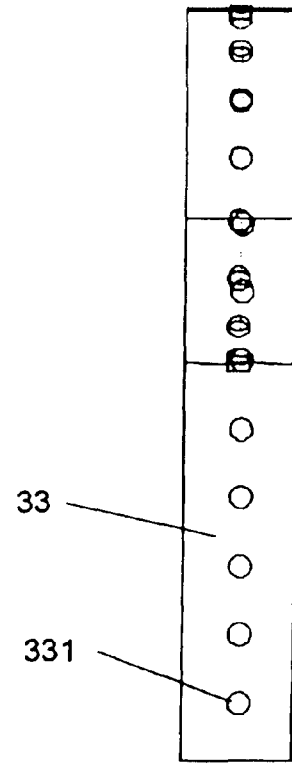
Fig. 4.b
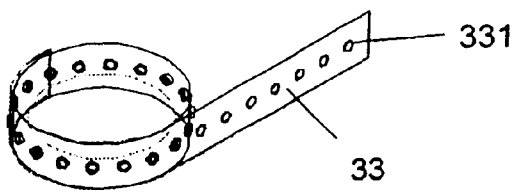
Fig. 4.c

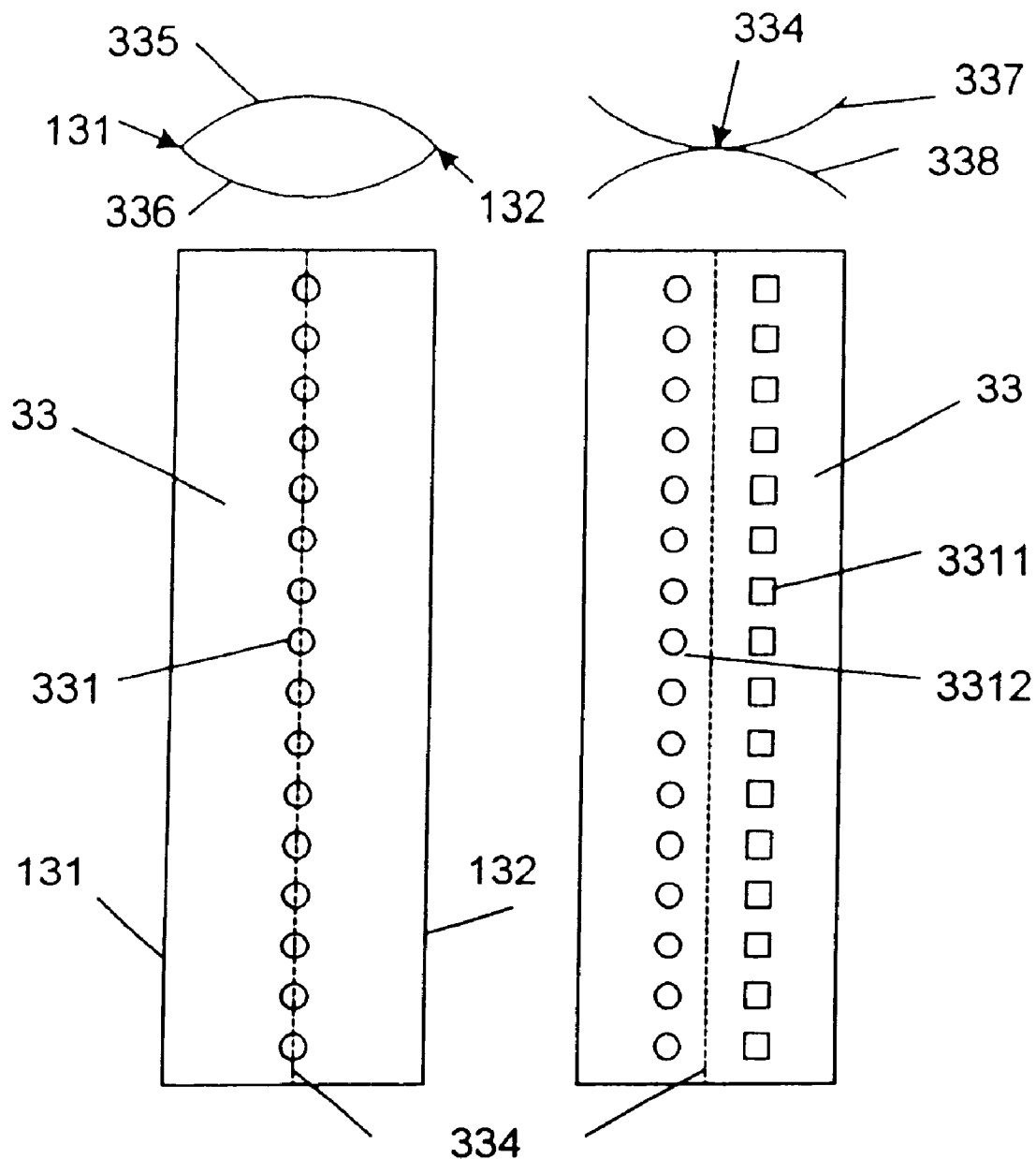
Fig. 6.a  Fig. 6.b

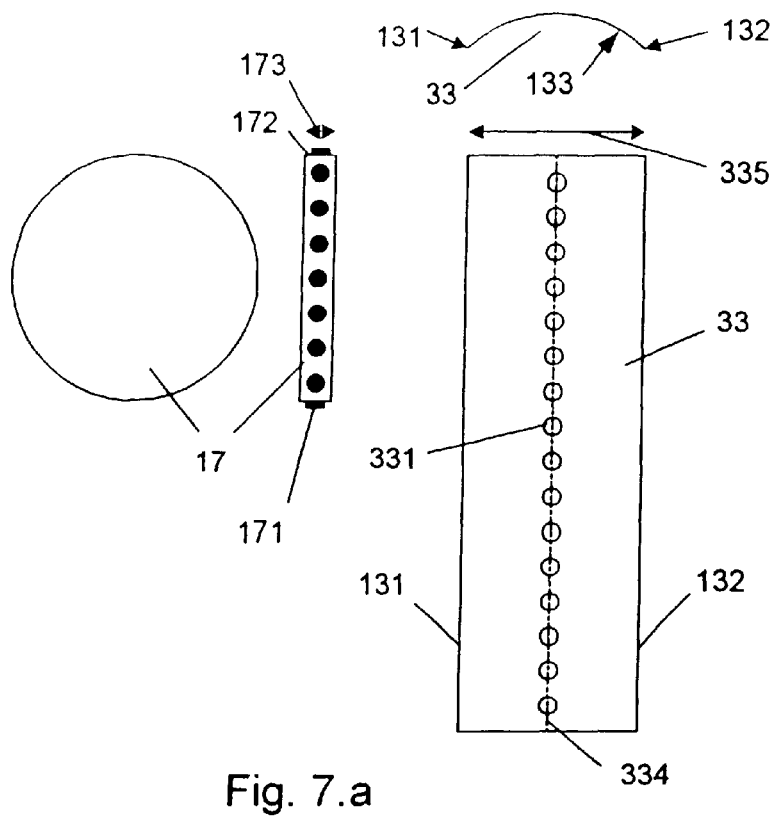
Fig. 7.a
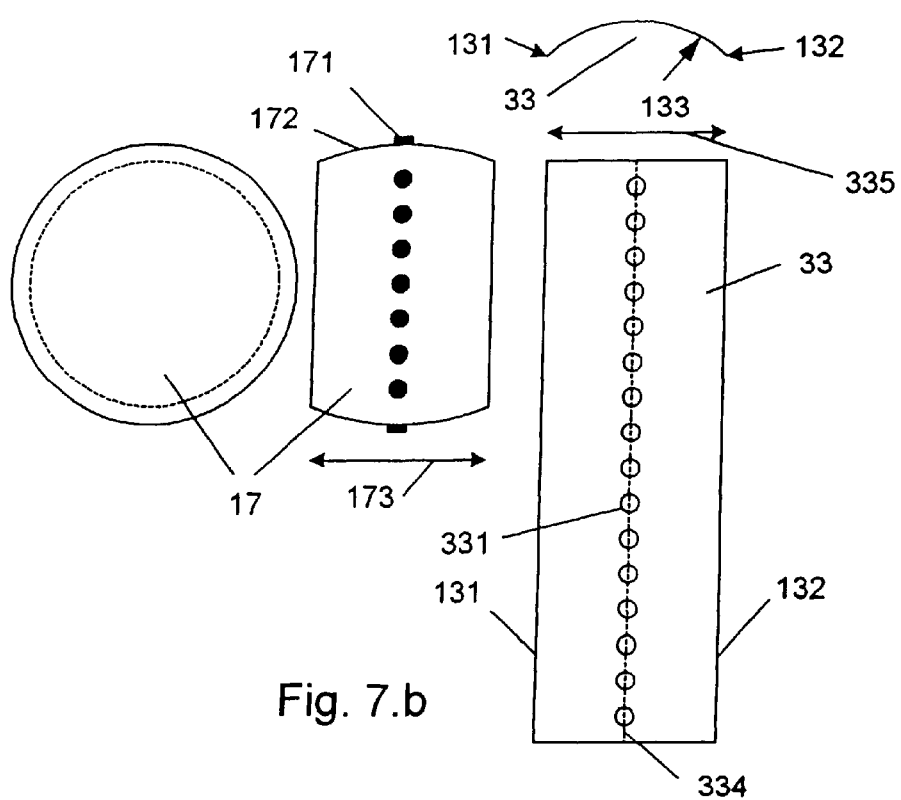
Fig. 7.b

MEDICATION DELIVERY DEVICE WITH BENDED PISTON ROD

This application claims the benefit of provisional application Ser. No. 60/240,898 filed Oct. 17, 2000.

THE TECHNICAL FIELD OF THE INVENTION

The invention relates to the design of medication delivery systems with a view to compactness, reliability, weight and production cost.

The invention relates specifically to: A portable medication delivery device comprising a medication cartridge having an outlet and a movable piston, and a housing for holding said cartridge, and a flexible piston rod being operable to engage and displace said piston along an axis of said cartridge, and guiding means for bending said piston rod away from said axis, and actuating means, and driving means for transferring movement from said actuating means to said piston rod, said driving means including a driving wheel for displacing the piston rod, said flexible piston rod comprising regularly spaced first members adapted to mechanically cooperate with corresponding second members on said driving wheel.

DESCRIPTION OF RELATED ART

The following account of the prior art relates to one of the areas of application of the present invention, medication delivery systems for self-treatment of a disease.

In a medication delivery system for self-treatment of a disease such as diabetes, safety and convenience in the handling of the injection or infusion are of major importance. One very important aspect of this is compactness of the device. Another very important aspect for a user is to ensure that a correct intended dose is delivered.

For the manufacturer of the devices aspects such as production control (testability) and economical solutions are important. A handy, i.e. small volume and lightweight, device that is highly reliable and at the same time economical in production is in demand.

U.S. Pat. No. 5,637,095 discloses a medication infusion pump with a flexible drive plunger comprising a spring tape. In one preferred form of the invention, the spring tape is wrapped or coiled onto a take-up spool within the pump housing. Drive means such as a drive capstan roller and associated pinch roller engage and advance the spring tape under control of the pump drive motor to correspondingly engage and advance the piston to deliver medication to the patient in a programmed manner.

EP-A-0 110 687 discloses a portable fluid infusion device including a flexible piston rod assembly. Attached to the piston is a flexible pusher tape, reversely bent in a U-shape at the upstream or open end of the syringe so that the distal end of the tape is adjacent to and in a position to ride upon the cylindrical body of the syringe as the piston is moved within the body of the syringe. The flexible pusher tape is made of a readily flexible plastics material such as a molded polypropylene. A series of parallel grooves are preformed in the face of the plastics tape along the narrow center portion thereof. The outwardly extending face of the tape is engaged by the helical drive screw at the part of the piston rod, which is deflected away from the axis of the cartridge. The rotation of the screw by a DC motor propels the tape in its U-shaped path to drive the piston.

DISCLOSURE OF THE INVENTION

The problems of the prior art are that the driving means are located relatively far from the piston and require a relatively thick piston rod having a relatively high friction with the housing and the cartridge, thus requiring a relatively high power consuming motor to advance it and possibly introducing inaccuracies in the displacement of the piston, or that the means for advancing the tape-shaped piston rod, the take-up spool storing the unused part of the tape, and the drum or wheel that supports the U-shaped path of the tape are individual self-contained functional units, yielding a relatively complex solution.

The object of the present invention is to provide a medication delivery system that combines compactness with an improved accuracy.

This is achieved according to the invention in that said flexible piston rod exhibits a linear or approximately linear path between said driving wheel and said piston.

In the present context, the term 'medication delivery system' is taken to mean an injector type device (such as a pen injector or a jet injector) for delivering a discrete dose of a liquid medication (possibly in the form of small drops) or a medication pump for continuous delivery of a liquid medication—in both cases optionally in combination with relevant electronic monitoring and control and possibly communications units.

In the present context the term 'piston' is taken to mean a displaceable plate or cylinder that fits tightly against the inner walls of a cartridge. A surface of the piston that faces the inner part of the cartridge and which may be brought into contact with the contents of the cartridge is termed 'the inner surface of the piston', and the opposite side of the piston is termed 'the outer surface of the piston'. In cooperation with a 'piston rod' that is engaged with 'the outer surface of the piston', the 'piston' may be displaced and used to apply pressure to a surface of the contents of the cartridge being in contact with 'the inner surface of the piston', thus e.g. delivering a dose through the outlet of the cartridge, if the piston is displaced in the direction towards the outlet. In the present context, the term 'piston' may also apply to a movable wall or membrane that engages with a plunger being an integral part of the piston rod.

In the present context, the term 'piston rod being operable to engage and displace said piston' is taken to mean that the piston rod may or may not be fixed to the movable wall, but that in both cases it has the ability to displace the piston at least in a direction towards the outlet of the cartridge.

In the present context, the term 'driving wheel' is taken to mean the part of the driving means that cooperates with the activating means (e.g. an electromotor) and the piston rod to transfer the movement of the activating means to a displacement of the piston rod. It may take the form of a gear wheel or drum or any other appropriate form that may be adapted to cooperate with the piston rod. A gear box may be inserted between the activating means and the driving wheel.

An advantage of having a linear path of the piston rod between the driving wheel and the piston is that the risk of introducing errors in the displacement of the piston by the rod is reduced because a more direct drive of the piston is provided (i.e. the sources of mechanical inaccuracies from a remotely located driving wheel due to the curved path, extra friction of the guiding means, etc. are eliminated). Related advantages of this are that an improved dose accuracy may be achieved and that the requirements with respect to the power of the activating means are reduced, leading to a possible reduction in weight and volume of the device.

A further improved dose accuracy may be achieved by combining the present invention with the invention disclosed in our co-pending patent application A medication delivery system with improved dose accuracy incorporated herein by reference.

Other advantages of the invention are that it uses a simple principle for transferring rotational movement of the actuating means to translatory movement of the piston rod, a principle that may be implemented in many different ways depending on the design constraints as regards space and materials. It allows the construction of a relatively compact medication device (utilizing e.g. a 180 degrees curve of the path of the piston rod), using a relatively thin piston rod yielding the benefits of a low weight and a potentially economical solution that is suited for large-scale production.

When said flexible piston rod remains in a fully reversible elastic state during cooperation with said driving wheel and said guiding means, it is ensured that the piston rod is able to adjust to the various curvatures of the driving and guiding means and cooperate therewith, without being irreversibly deformed.

When the surface of said flexible piston rod in a transversal cross-section is adapted to follow the surface of said driving wheel fully or partially, it is ensured that the change of the cross-section of the piston rod during its bending cooperation with the driving and guiding means is accounted for to ensure a seamless cooperation between the rod and the driving and guiding means.

When said guiding means also work as a take-up spool for storing the unused part of the piston rod, it is ensured that an especially compact and economical solution is provided.

When said driving wheel and said guiding means are the same physical unit, it is ensured that an especially simple, compact and economical solution is provided.

When said driving wheel is located after said guiding means in a downstream direction towards said cartridge, it is ensured that the driving means are located as close as possible to the piston to be displaced, thus minimizing the sources of errors and improving dose accuracy.

In the present context, the term 'downstream' is taken to mean in a direction of the movement of the piston when medication is expelled from the cartridge, said direction also defining a 'longitudinal direction' of the piston rod.

When said piston rod touches the inner walls in an axial direction of said cartridge at one or more points in a transversal cross-section of said piston rod, it is ensured that the ability of the rod to withstand an axial pressure is improved.

In the present context 'the inner walls of the cartridge' are taken to mean the interior surfaces of the walls of the cartridge being in contact with the medication. 'A transversal cross-section of the piston rod' is taken to mean a cross-section of the rod that is perpendicular to the longitudinal direction of the piston rod, i.e. for the part of the rod between the driving wheel and the piston, a direction perpendicular to the direction defined thereby (i.e. perpendicular to the axial direction of the cartridge).

When the longitudinal edges of said piston rod in the cartridge touch the inner walls of said cartridge, it is ensured that the piston rod is guided when displacing the piston in the cartridge, improving the ability to withstand an axial pressure.

In the present context the term 'the longitudinal edges of said piston rod in the cartridge' refers to the edges of the rod in a direction defined by the longitudinal direction of the piston rod.

When said flexible piston rod is tape-shaped, it is ensured that a solution that is convenient from a production point of view and which is well suited for coiling is provided, and that an improved flexibility in the physical design of the medication delivery system is introduced.

In the present context the term 'tape-shaped' in connection with 'piston rod' is taken to mean that the cross-section of the rod perpendicular to its longitudinal direction is 'wider' than its 'height'. It does not have to take the form of a rectangular cross-section but could be grooved or toothed or wave-shaped or convex or concave or something else that might be convenient from a design point of view.

When said flexible piston rod consists of two separate tape-shaped bodies that are joined together at one or more points in a transversal cross-section, it is ensured that a greater axial pressure may be applied to the rod compared to a 'single layer' solution, in other words that thinner materials may be used, resulting in lower weight and reduced costs and thus a greater degree of freedom in the design of the medication delivery device. Further, the piston rod may be subject to a sharper bend than a corresponding one-layer rod. A tape-shaped piston rod that is sufficiently stiff in itself (i.e. without touching the inner walls of the cartridge) may thus be provided.

In a preferred embodiment said two separate tape-shaped bodies are joined together in the central point of a transversal cross-section.

In a preferred embodiment the distance between said two tape-shaped bodies increases with increasing distance from said central point when viewed in a transversal cross-section in a relaxed state.

In the present context the term 'in a relaxed state' refers to a situation in which no external forces (other than gravity) are applied to the rod.

When said two separate tape-shaped bodies are joined together at the edges of a transversal cross-section, it is ensured that an economical and light-weight solution that is well suited for production in larger quantities is provided, and which may be bent around a relatively smaller minimum radius of curvature.

In a preferred embodiment, said edges are joined by applying a coating layer to the surface of said separate tape-shaped bodies. This has the advantage (in addition to joining the two bodies by forming a continuous and flexible hinge between their corresponding longitudinal edges) of yielding a very even surface of the rod and provides the possibility of applying a coating that is especially appropriate for the application in question, e.g. that it minimizes friction, that it improves corrosion resistance, etc.

In a preferred embodiment said two tape-shaped bodies describe an eye-shaped path when viewed in a transversal cross-section in a relaxed state.

In a preferred embodiment said first members on said flexible piston rod comprise protruding members and said corresponding second members on said driving wheel comprise receiving members. In an embodiment thereof, the driving wheel comprises e.g. regularly spaced indentations that interact with corresponding protrusions on the piston rod to displace the piston rod. This has the advantage that the protrusions are 'hidden' in the driving wheel when the piston rod engages the wheel, possibly reducing the free space needed around the driving wheel (thus minimizing the volume of the construction).

In a preferred embodiment said first members comprise receiving members and said corresponding second members comprise protruding members.

In a preferred embodiment said first members comprise individually isolated indentations and said corresponding second members comprise individually isolated projecting members.

When said first members comprise individually isolated through holes and said corresponding second members comprise individually isolated projecting members, it is ensured that a secure grip between piston rod and driving wheel is provided.

In a preferred embodiment said regularly spaced members are located along a centerline in the longitudinal direction of said flexible piston rod.

When said first members comprise individually isolated cuts located at least along one periphery in the longitudinal direction of said flexible piston rod and said corresponding second members comprise individually isolated projecting members, it is ensured that a secure grip between piston rod and driving wheel is provided. Further, a greater axial stiffness of the rod is achieved.

When the piston rod is at least partially made of a plastics material, it is ensured that a solution combining the benefits of using a plastics material (e.g. corrosion resistance) with those of other materials (e.g. greater mechanical stability, stiffness, etc.) may be provided.

In a preferred embodiment the piston rod is at least partially made of a metallic material.

BRIEF DESCRIPTION OF THE DRAWINGS

The invention will be explained more fully below in connection with a preferred embodiment and with reference to the drawings, in which.

The figures are schematic and simplified for clarity, and they just show details which are essential to the understanding of the invention, while other details are left out. Throughout, the same reference numerals are used for identical or corresponding parts.

DETAILED DESCRIPTION OF EMBODIMENTS

Figure 1:
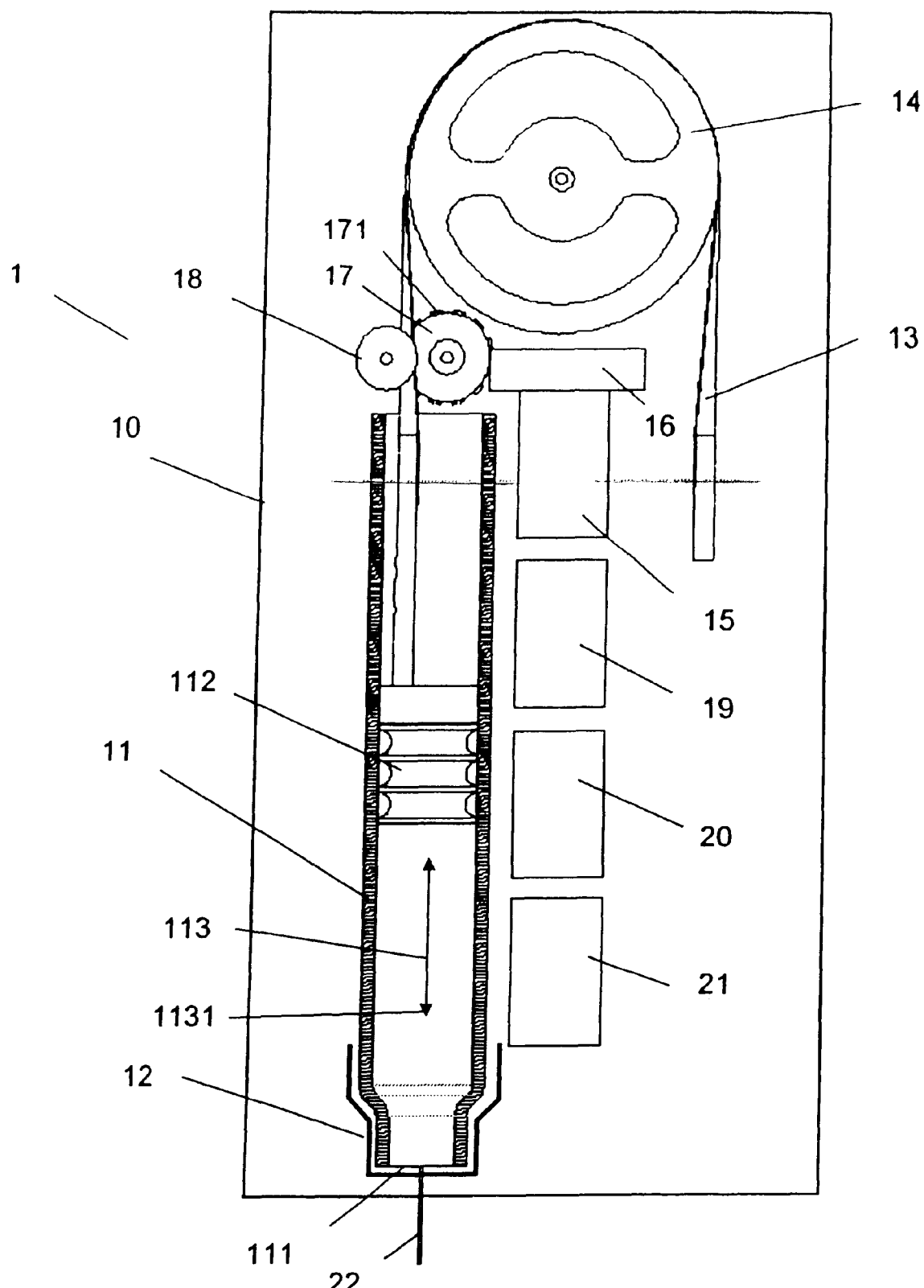
FIG. 1 shows a medication delivery system according to the invention where the driving wheel is located next to the medication cartridge, FIGS. 2.a–2.b show an embodiment of the invention where driving wheel and guiding means are one physical unit, FIGS. 3.a–3.d show various embodiments of a tape-shaped piston rod according to the invention, FIGS. 4.a–4.c show a tape-shaped piston rod and corresponding driving wheel according to the invention for which a coiling of the tape on the driving wheel is possible.

FIG. 1 shows a medication delivery system according to the invention where the driving wheel is located next to the medication cartridge.

In the embodiment of the medication delivery system 1 in FIG. 1, a medication cartridge 11 (possibly a replaceable one) with a piston 112 and an outlet 111 to which a needle 22 (possibly replaceable) may be fixed, is shown to cooperate with a piston rod 13 in the form of a tape, the tape being arcuate (cf. correspondingly FIG. 2.b) in a transversal cross-section. The cartridge 11 is removably fixed to a cartridge holder 12. The piston rod 13 may be displaced along a longitudinal axis 113 of the cartridge 11. A downstream direction is defined by the arrow 1131. The movement of the piston rod 13 is activated by an electromotor 15 whose rotational movement is transferred to a linear displacement of the piston rod by suitable driving means, the driving means comprising inter alia a driving wheel 17 with regularly spaced protruding members 171 that are adapted to cooperate with corresponding regularly spaced openings (cf. 331 in FIGS. 3.c and 3.d) on the piston rod. The piston rod 13 is bent to make a 180 degrees U-turn over a first guiding wheel 14. A second guiding wheel 18 ensures a proper contact between the piston rod and the driving wheel 17. In the embodiment of FIG. 1, the faces of the second guiding wheel 18 and the driving wheel 17 that receive the tape-shaped piston rod 13 have a concave face and a corresponding convex face, respectively. This has the effect that the piston rod acquires its normal arcuate form in a transversal direction of the rod appropriately adjusted lo the diameter of the medication cartridge (e.g. so that the edges of the piston rod (and not the central part of the rod) touch the inner walls of the cartridge (cf. FIG. 2.b). The receiving faces of the guiding wheels 14, 18 and driving wheel 17 may of course take other forms that are convenient from a design point of view.

In an embodiment of the invention, the piston rod 13 is adapted to elastically adjust fully or partially to the shape of the surfaces of the driving wheel 17 and the guiding wheel 14 along its path of contact with said wheels. Alternatively, the surfaces of the wheels are adapted to match fully or partially the shape of the side of the piston rod that engages with the wheels when the piston rod is bent around the wheel in question. This applies to the longitudinal as well as the transversal directions of the rod. In the longitudinal direction, the smallest diameter of the wheel is limited by the smallest diameter around which the rod may be elastically bent (i.e. reversibly). In the transversal direction, for the embodiment in FIG. 6.a, for example, this means that the eye-shaped cross-sectional view 'collapse' to a shape that follows the wheel in question.

In another embodiment of the invention, the width of the driving wheel (and possible guiding wheels) is smaller than the width of the tape-shaped rod when viewed in a transversal cross-section (cf. FIG. 7.a). In this case, a piston rod with centrally located (cf. e.g. FIG. 3.a, 3.c or 6.a) or nearly centrally located (cf. FIG. 3.d or 6.b) is used.

In an embodiment of the invention said first guiding wheel 14 is substituted by a fixed guideway (providing an equivalent bending of the piston rod), optionally coated with a layer that ensures a low friction between guideway and piston rod. The transversal cross-section of the guideway is adapted to match fully or partially the shape of the side of the piston rod that engages with the guideway when the piston rod is bent around it during its normal operation.

When the medication cartridge is replaceable, it is ensured that the major part of the medication device may be used again and again only by inserting a new cartridge (and possibly a new needle in the case of an injection device) when the contents of the medication cartridge has been ejected or when another medication is to be used, i.e. e.g. in the situation of a person's self-treatment of a disease (e.g. diabetes) that requires frequent delivery of medication (e.g. insulin) over an extended period of time. If the replaceable cartridge contains a fully functioning piston (and possibly a corresponding piston rod), a convenient and flexible solution is provided, where the medication cartridge may be replaced in a quick and hygienically safe way.

To ensure that the piston rod follows the guiding wheel 14 along the relevant part thereof, the 'upstream' end of the piston rod (i.e. the end of the rod that does not engage the piston) may be connected to a part of the medication device that is held fixed relative to the cartridge by a salient element (e.g. a spring, not shown) whose one end is tied to the piston rod and whose other end is held fixed.

Typically, the medication delivery process including analysis and use of historical data concerning the device and user in question, diagnostic proposals, error correction, etc. is governed by appropriate processing and communications units.

In the embodiment in FIG. 1.*a* the driving means include appropriate means 16 for transferring movement from the electromotor 15 to the driving wheel 17, e.g. in the form of a gear box. The electromotor is controlled by a processing unit 19 (including relevant memory means). The processing unit 19 may exchange information with the user and other systems via I/O-means 20 (comprising e.g. a display, keypad, and relevant communications interfaces). The electronic units are powered from the energy source 21 (e.g. a battery pack or an interface to external energizing means).

A housing 10 for protecting and optionally supporting the piston rod at its 180 degrees path and for covering the electromotor and other vital parts of the device is provided.

Figure 5:
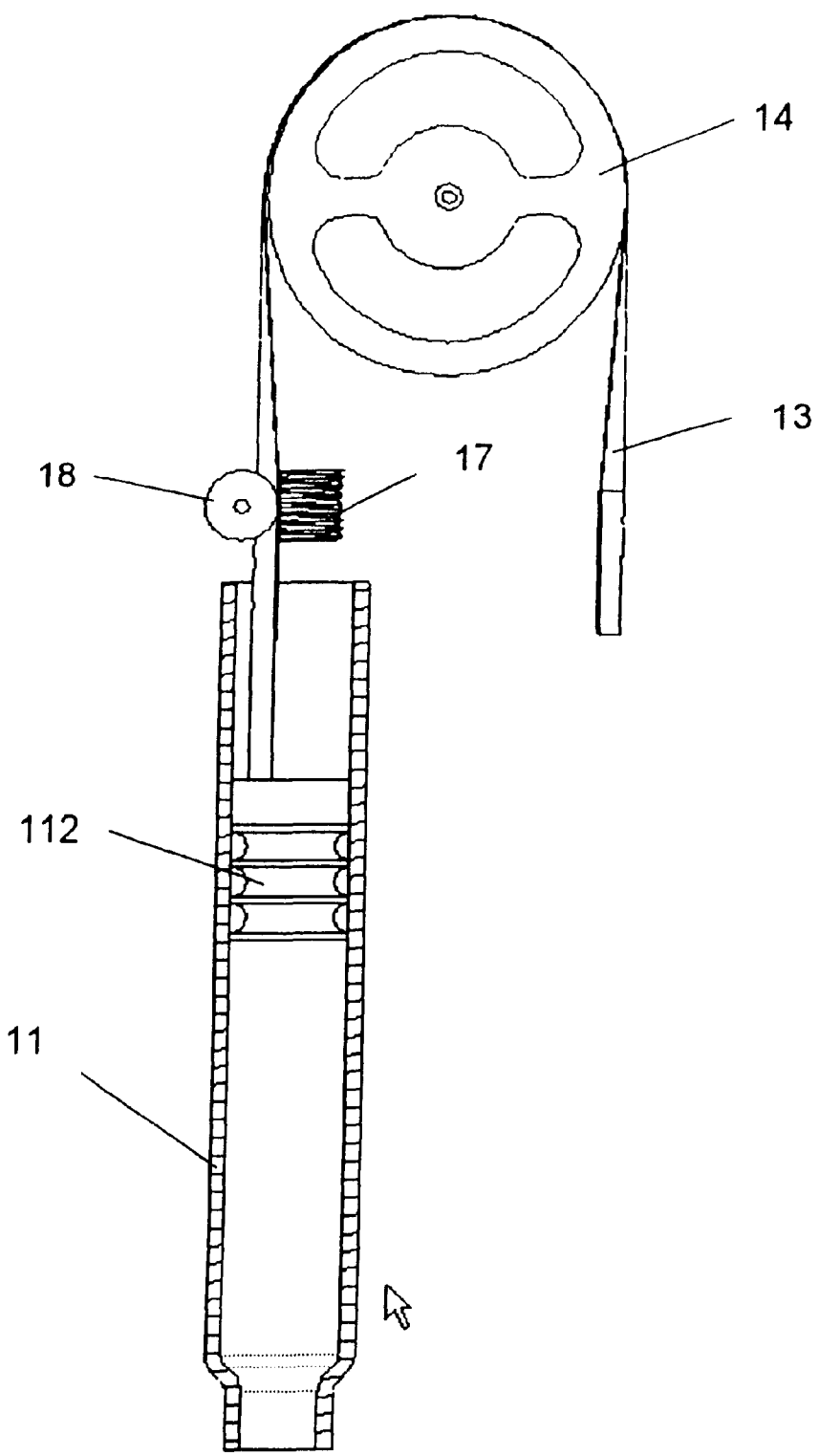
FIG. 5 shows a medication delivery system according to the invention where the driving wheel in the form of a screw is located between the guiding means and the medication cartridge, FIGS. 6.a–6.b show some possible designs of a piston rod according to the invention, and FIGS. 7.a–7.b show some possible designs of a piston rod and a driving drum according to the invention.

The housing 10, the cartridge holder 12, the means 16 for transferring movement from the electromotor to the driving wheel, the electromotor 15, the processing unit 19, the I/0-means 20 and the energy source 21 are not included in FIGS. 2 and 5, but are implied.

FIGS. 2.*a*–2.*b* show an embodiment of the invention where driving wheel and guiding means are one physical unit.

In FIG. 2.*a* only the central features of the invention are illustrated. FIG. 2.*a* shows a driving wheel 17 with regularly spaced teeth 171 that cooperate with corresponding indentations on the piston rod 13. When the driving wheel 17 is activated in a counterclockwise direction by the actuating means (not shown), the piston rod 13 is displaced in a downstream direction and acts to displace the piston 112 to expel medication from the cartridge 11 through the outlet 111 and an attached needle (not shown). By allowing the driving wheel to create the 180 degrees bending of the piston rod, a particularly simple embodiment is provided. Additionally, this embodiment is more compact and lighter.

FIG. 2.*b* shows a cross-sectional view of the medication cartridge 11 and the piston rod 13 along the line BB. The curved cross-section of the piston rod 13 is apparent. The edges 131, 132 of the tape-shaped piston rod glide on the inner walls of the cartridge 11, yielding a mechanically more stable construction in that a greater force may be applied to the tape rod, without it bending out of the linear path from the edge of the driving wheel to the point of engagement of the piston rod with the piston.

FIGS. 3.*a*–3.*d* show various embodiments of a tape-shaped piston rod according to the invention.

FIG. 3.*a* shows an embodiment of a tape-shaped piston rod 33 with parallel grooves 330 in a transversal (or nearly transversal) direction of the tape-shaped piston rod in a central part on the side of the tape that cooperates with a corresponding driving screw (cf. 17 in FIG. 5). The grooves may optionally extend through the material to form slots for cooperation with corresponding threads on the driving wheel.

FIG. 3.*b* shows an embodiment of a tape-shaped piston rod 33 with regularly spaced cut-outs 332 in each of the longitudinal edges of the tape for cooperation with corresponding projecting pins on the driving wheel (not illustrated). Put differently, the tape-shaped piston rod is provided with regularly spaced projecting members along its longitudinal edges and the driving wheel has corresponding receiving members to provide a secure grip of the piston rod when the rod engages with the driving wheel. This embodiment yields a very good grip between tape and wheel and a very accurate positioning in a transversal direction of the tape, both contributing to a more accurate dosage. It further provides a piston rod that is able to withstand a larger axial pressure (without bending) than corresponding solutions depicted in FIGS. 3.*c* and 3.*d*.

FIG. 3.*c* shows an embodiment of a tape-shaped piston rod 33 with regularly spaced, centrally located rectangular through holes 331 in the tape for cooperation with corresponding projecting pins on the driving wheel (e.g. 171 in FIGS. 1 and 2).

FIG. 3.*d* shows an embodiment of a tape-shaped piston rod 33 with two rows of regularly spaced, circular through holes 331 located symmetrically around the longitudinal centre line of symmetry of the tape for cooperation with corresponding projecting pins on the driving wheel (not shown).

FIGS. 4.*a*–4.*c* show a tape-shaped piston rod and corresponding driving wheel according to the invention for which a coiling of the tape on the driving wheel is possible.

The piston 33 comprises a tape with centrally situated, regularly spaced circular holes 331 adapted to cooperate with corresponding protruding circular cylindrical members 361 on the driving drum 36. The driving drum is activated by an electromotor (not shown) through appropriate driving means (e.g. a gear box, not shown). The holes are shown to be positioned along a centerline of the tape, but may of course be located at one or both longitudinal edges of the tape (cf. FIG. 3.*b*) or along a line off the centre line or in any other convenient way as long as the protruding means on the driving drum follow a corresponding pattern. Likewise, the individual holes and corresponding protruding members may take on any convenient form, e.g. edged as opposed to circular, as long as the holes in the tape and the protruding members on the driving drum correspond.

FIGS. 4.*a* and 4.*b* show orthogonal plane views of the piston rod and driving drum, whereas FIG. 4.*c* shows a perspective view of a coiled piston rod and illustrate the fact that the unused part of the tape/piston rod may be stored on the driving drum, yielding a simple and compact solution.

FIG. 5 shows a medication delivery system according to the invention where the driving wheel in the form of a screw is located between the guiding means and the medication cartridge.

FIG. 5 shows a driving screw 17 that cooperates with corresponding grooves (cf. 330 in FIG. 3.*a*) on the piston rod 13. When the driving wheel 17 is activated by the actuating means (not shown), the piston rod 13 is displaced in a downstream direction and acts to displace the piston 112 to expel medication from the cartridge 11 through the outlet and an attached needle (not shown). The piston rod makes a 180 degrees bend over a guiding wheel 14. A second guiding wheel 18 ensures a proper contact between the piston rod and the driving screw 17.

FIG. 6 shows some possible designs of a piston rod according to the invention.

The piston rod may be made in many different forms according to design requirements (materials, stiffness, weight, corrosion, etc.) and cost. The rod may be made of one longitudinal piece of material or alternatively be composed of several layers joined together at one or more points in a transversal cross-section of the tape. In the longitudinal direction, the tape may be joined together in isolated (possibly regularly spaced) 'points' or continuously. The joining may be performed by welding or adhesive techniques or any other appropriate joining technique.

FIG. 6.a shows a preferred embodiment of a tape-shaped piston rod 33, where the rod is made of two identical longitudinal pieces 335, 336 of foil that are joined together along their edges 131, 132 and have centrally located 334, regularly spaced openings 331 for cooperation with a driving wheel. The two individual pieces of tape have an arcuate cross-section in a relaxed state, thus forming an eye-shaped cross-section when joined at the edges. In a preferred embodiment the individual pieces of tape are made of a salient metallic material of 0.5 mm thickness and the joining is achieved by coating the outer surface with a ductile polymer layer. If appropriate, the layer may be applied to the inner surfaces of the rod or only along the joining lines of the rod. Alternatively, a ductile adhesive tape may be applied along the joining lines of the rod.

In another preferred embodiment, as depicted in FIG. 6b, the rod 33 is made of two identical longitudinal pieces 337, 338 of foil that are joined together along their centre lines 334 to give an X-shaped cross-section and having two rows of regularly spaced holes 3311, 3312 for cooperation with a driving wheel. The holes are located on each side of the central point of the tape when viewed in a transversal cross-section of the rod. The holes are shown to be circular and quadratic, respectively, but they may take any form that is appropriate for cooperation with a driving wheel. Likewise indentations may be used depending on material thickness as long as a sufficient grip with the driving wheel is ensured.

FIGS. 7.a–7.b show some possible designs of a piston rod and a driving drum according to the invention.

FIG. 7.a shows an embodiment of the invention where the driving drum 17 with regularly spaced projecting pins 171 has a width 173 in the direction of its axis of symmetry that is much smaller than the width 335 of the tape-shaped piston rod 33. The piston rod 33 has regularly spaced openings 331 located along a centre line 334 adapted to cooperate with the projecting pins 171 of the driving drum 17. The piston rod has longitudinal edges 131, 132. The piston rod has an arcuate transversal cross-section in a relaxed state. The surface 172 of the driving drum facing the corresponding surface 133 of the piston rod (shown in FIG. 7.a in its relaxed state) is flat (linear as opposed to arcuate), but may take any convenient form as long as its width 172 is sufficiently small compared to the width 335 of the rod and the projecting pins provide a sufficient grip with the openings of the piston rod.

FIG. 7.b shows an embodiment of the invention where the driving drum 17 with regularly spaced projecting pins 171 has a width 173 in the direction of its axis of symmetry that is comparable to the width 335 of the tape-shaped piston rod 33. Again, the piston rod 33 has regularly spaced openings 331 located along a centre line 334, the rod having longitudinal edges 131, 132. The openings 331 are adapted to cooperate with the projecting pins 171 of the driving drum 17. The piston rod has an arcuate transversal cross-section in a relaxed state. The surface 172 of the driving drum facing the corresponding surface 133 of the piston rod is arcuate and adapted to match the curvature of the piston rod fully or partially in a transversal cross-section, when the rod is brought into contact with and forced to follow a radial path of the drum (i.e. when the projecting pins of the drum cooperate with the openings of the piston rod). The arcuate surface 133 of the piston rod in a relaxed state is shown in FIG. 7.b. In general, the radius of curvature of the surface 172 of the driving drum contacting the piston rod is greater than the radius of curvature of the corresponding surface 133 of the transversal cross-section of the piston rod in a relaxed state, as indicated in FIG. 7.b. In a special embodiment the radius of curvature of the surface 172 of the driving drum contacting the piston rod is infinite (i.e. the surface is linear).

The piston rod and driving and guiding members should be designed in such a way that the piston rod, when cooperating with the said members, remains in a fully reversible, elastic mode of deformation (in its longitudinal as well as its transversal cross-sections). This may be achieved by a proper choice of materials and geometrical dimensions.

Some preferred embodiments have been shown in the foregoing, but it should be stressed that the invention is not limited to these, but may be embodied in other ways within the subject-matter defined in the following claims.

What is claimed is:

1. A portable medication delivery device comprising a medication cartridge having an outlet and a movable piston, and a housing for holding the cartridge, and a flexible piston rod being operable to engage and displace the piston along an axis of the cartridge, and a guiding means for bending the piston rod away from the axis, and an actuating means and driving means for transferring movement from the actuating means to the piston rod, the driving means including a driving wheel for displacing the flexible piston rod, the flexible piston rod comprising regularly spaced first members adapted to mechanically cooperate with corresponding second members on the driving wheel, wherein: the flexible piston rod comprises at least two separate tape-shaped bodies that are joined together at one or more points in a traversal cross-section.

2. The medication delivery device of claim 1, wherein the at least two separate tape-shaped bodies are joined together in a central point of the traversal cross section.

3. The medication delivery device of claim 2, wherein the distance between the two tape-shaped bodies increases with increasing distance from the central point when viewed in a traversal cross-section in a relaxed state.

4. The medication delivery system of claim 1, wherein the at least two separate tape-shaped bodies are joined together at the edges of the traversal cross-section.

5. The medication delivery system of claim 4, wherein the edges are joined by applying a layer to the surface of the separate tape-shaped bodies.

6. The medication delivery system of claim 4, wherein the two tape-shaped bodies describe an eye-shaped path when viewed in a traversal cross-section in a relaxed state.

7. The medication delivery system of claim 1, wherein the first members on the flexible piston rod comprise protruding members and the corresponding second members on the drive wheel comprise receiving members.

8. The portable medication delivery system of claim 1, wherein the first members comprise receiving members and the corresponding second members comprise protruding members.

9. The medication delivery device of claim 8, wherein the first members comprise individually isolated indentations and the corresponding second members comprise individually isolated projecting members.

10. The medication delivery device of claim 8, wherein the first members comprise individually isolated through holes and the corresponding second members comprise individually isolated projecting members.

11. The medication delivery device of claim 7, wherein the regularly spaced members are located along a center line in the longitudinal direction of the flexible piston rod.

12. The medication delivery device of claim 8, wherein the first members comprise isolated cuts located at least along one periphery in the longitudinal direction of the flexible piston rod and the corresponding second members comprise individually isolated projecting members.

13. The medication delivery device of claim 1, wherein the piston rod is at least partially made of a plastic material.

14. The medication delivery device of claim 1, wherein the piston rod is at least partially made of a metallic material.

15. The medication delivery device of claim 1, wherein the piston rod touches an inner wall in an axial direction of the cartridge at one or more points in the traversal cross-section of the piston rod.

16. The medication delivery device of claim 15, wherein the longitudinal edges of the piston rod in the cartridge touch the inner walls of the cartridge.

17. A flexible piston rod for a medication delivery device comprising two separate tape-shaped bodies joined together at one or more points in a traversal cross section.

18. The flexible piston rod of claim 17 wherein the two tape-shaped bodies are joined together in a central point of the traversal cross-section.

19. The flexible piston rod of claim 17 wherein the two tape-shaped bodies are joined together at edges of the traversal cross-section by applying a coating layer to the surface of each tape-shaped bodies.

* * * * *